US012758959B2

(12) United States Patent
Gong et al.

(10) Patent No.: US 12,758,959 B2
(45) Date of Patent: Oct. 13, 2026

(54) SUPPORTED POLYMETALLIC OXIDE TANDEM CATALYST, PREPARATION METHOD AND APPLICATION THEREOF

(71) Applicant: TIANJIN UNIVERSITY, Tianjin (CN)

(72) Inventors: Jinlong Gong, Tianjin (CN); Wei Wang, Tianjin (CN); Sai Chen, Tianjin (CN); Chunlei Pei, Tianjin (CN); Zhijian Zhao, Tianjin (CN)

(73) Assignee: TIANJIN UNIVERSITY, Tianjin (CN)

( * ) Notice: Subject to any disclaimer, the term of this patent is extended or adjusted under 35 U.S.C. 154(b) by 194 days.

(21) Appl. No.: 18/601,509

(22) Filed: Mar. 11, 2024

(65) Prior Publication Data

US 2024/0307861 A1 Sep. 19, 2024

(30) Foreign Application Priority Data

Mar. 15, 2023 (CN) ......................... 202310248877.1

(51) Int. Cl.
*B01J 37/02* (2006.01)
*B01J 21/04* (2006.01)
(Continued)

(52) U.S. Cl.
CPC ............. *B01J 37/024* (2013.01); *B01J 21/04* (2013.01); *B01J 21/063* (2013.01); *B01J 21/08* (2013.01);
(Continued)

(58) Field of Classification Search
CPC ........ B01J 37/024; B01J 21/04; B01J 21/063; B01J 21/08; B01J 23/06; B01J 23/08; B01J 23/22; B01J 23/26; B01J 23/34; B01J 23/8472; B01J 29/076; B01J 37/009; B01J 37/0236; B01J 37/088; B01J 23/002; B01J 23/862; B01J 29/00; B01J 2523/00; B01J 35/00; B01J 35/30; B01J 35/50; B01J 23/86; C07C 5/324; C07C 2521/04; C07C 2521/06; C07C 2521/08; C07C 2523/06;
(Continued)

(56) References Cited

U.S. PATENT DOCUMENTS

| | | | | |
|---|---|---|---|---|
| 6,787,023 | B1 * | 9/2004 | Mohr | B01J 29/7415 502/64 |
| 2017/0233312 | A1 * | 8/2017 | Hossain | C07C 5/42 585/656 |
| 2020/0306734 | A1 * | 10/2020 | Arshad | B01J 23/8472 |

* cited by examiner

*Primary Examiner* — Vishal V Vasisth
*Assistant Examiner* — Francis C Campanell

(57) ABSTRACT

The present disclosure discloses a supported polymetallic oxide tandem catalyst, preparation method and application thereof, a surface of the support is supported with an oxide of metal A and then with metal vanadate nano-particles; and the oxide of metal A serves as a direct dehydrogenation catalytic site, and the metal vanadate nano-particles serve as a selective hydrogen combustion site. In the application of the tandem catalyst, dehydrogenation site and selective hydrogen combustion site are coupled at the nano-scale, and this coupling mechanism shifts the reaction equilibrium to the alkenes through the selective combustion of byproduct hydrogen, which effectively surpasses the thermodynamic limit; and meanwhile, the combustion of hydrogen releases chemical energy, and provides heat energy through direct heating, enabling the self-heating operation of the reaction. The present disclosure has the outstanding advantages of high single-pass conversion rate of light alkanes and high selectivity towards target product alkenes.

3 Claims, 5 Drawing Sheets

(51) Int. Cl.

| | |
|---|---|
| ***B01J 21/06*** | (2006.01) |
| ***B01J 21/08*** | (2006.01) |
| ***B01J 23/06*** | (2006.01) |
| ***B01J 23/08*** | (2006.01) |
| ***B01J 23/22*** | (2006.01) |
| ***B01J 23/26*** | (2006.01) |
| ***B01J 23/34*** | (2006.01) |
| ***B01J 23/847*** | (2006.01) |
| ***B01J 29/076*** | (2006.01) |
| ***B01J 37/00*** | (2006.01) |
| ***B01J 37/08*** | (2006.01) |
| ***C07C 5/32*** | (2006.01) |

(52) U.S. Cl.

CPC ............... *B01J 23/06* (2013.01); *B01J 23/08* (2013.01); *B01J 23/22* (2013.01); *B01J 23/26* (2013.01); *B01J 23/34* (2013.01); *B01J 23/8472* (2013.01); *B01J 29/076* (2013.01); *B01J 37/009* (2013.01); *B01J 37/0236* (2013.01); *B01J 37/088* (2013.01); *C07C 5/324* (2013.01); *C07C 2521/04* (2013.01); *C07C 2521/06* (2013.01); *C07C 2521/08* (2013.01); *C07C 2523/06* (2013.01); *C07C 2523/08* (2013.01); *C07C 2523/22* (2013.01); *C07C 2523/26* (2013.01); *C07C 2523/34* (2013.01); *C07C 2523/745* (2013.01); *C07C 2523/847* (2013.01); *C07C 2529/076* (2013.01)

(58) Field of Classification Search

CPC ............ C07C 2523/08; C07C 2523/22; C07C 2523/26; C07C 2523/34; C07C 2523/745; C07C 2523/847; C07C 2529/076; C07C 5/54; C07C 5/3332; Y02P 20/52

USPC .......................................................... 585/663

See application file for complete search history.

SUPPORTED POLYMETALLIC OXIDE TANDEM CATALYST, PREPARATION METHOD AND APPLICATION THEREOF

CROSS-REFERENCE TO RELATED APPLICATION

This application claims priority from the Chinese patent application 2023102488771 filed Mar. 15, 2023, the content of which is incorporated herein in the entirety by reference.

TECHNICAL FIELD

The present disclosure relates to the field of tandem catalysts, in particular to a tandem catalyst for light alkane dehydrogenation and chemical looping-selective hydrogen combustion, a preparation method and an application thereof.

BACKGROUND

Propylene, one of the three basic raw materials of the synthetic materials, cannot meet the market demand and the low-carbon economic strategy due to disadvantages such as high energy consumption, large carbon emission produced by the traditional production technologies (light oil cracking and heavy oil catalytic cracking). Meanwhile, with the rapid growth of the propylene downstream product chain, propylene supply requirements continue to expand in the global range. Therefore, the development of the novel propylene production technology is impending. Propane dehydrogenation (PDH) as a novel method of on-purpose propylene production is widely concerned; however, PDH is a highly endothermic reaction limited by thermodynamic equilibrium. At present, an external indirect heating mode is usually adopted in industrial production, but still exists problems such as requiring ultra-high temperature and low heat transfer efficiency. In order to improve the equilibrium conversion of PDH, strategies of high reaction temperature, low reaction pressure or dilution of feed gas are generally used. However, the implementation of the above strategies tend to introduce additional operating costs, accelerate side reactions, and induce deactivation of the catalyst.

View from the perspective of energy supply, the SMART styrene production process according to U.S. Pat. No. 4,812,597 provides a good design sample for a segmented alternate dehydrogenation reactor and a hydrogen combustion reactor. The dehydrogenation catalyst in the dehydrogenation reactor is responsible for producing hydrocarbon species and hydrogen such as ethylbenzene/styrene in the reactant stream after ethylbenzene is partially dehydrogenated, and then the reactant stream is switched to the hydrogen combustion reactor, and the hydrogen combustion catalyst is subjected to hydrogen combustion selectivity in the presence of hydrocarbon species such as ethylbenzene/styrene in an oxygen atmosphere. The energy generated by hydrogen combustion is used to increase the temperature of the stream in a direct heating manner to the temperature at which the dehydrogenation reaction can occur to remove hydrogen again, thereby replacing the traditional inter-segment indirect heating mode. However, oxygen co-feeding increases economic costs and potential safety hazards to some extent. Prof. Grasselli et al. discloses a method of physical mixing two different catalysts in a single catalyst bed, hydrogen combustion selectivity is achieved by utilizing the lattice oxygen of the metal oxide under the condition of no oxygen co-feeding, which is a win-win method. However, the adopted metallic oxide is poor at cyclic regeneration, for example, bismuth oxide generates the bismuth in the metal state after being reduced, and the lower melting point (271° C.) causes the reduction state metal bismuth to easily volatilize to cause loss. Therefore, a metal oxide with low cost, high stability and high hydrogen combustion selectivity as a solid oxygen carrier to be coupled with a propane dehydrogenation catalyst is required and has a strategic research value.

SUMMARY

The present disclosure aims to solve the related technical problems of the application of tandem catalysts to light alkane dehydrogenation and chemical looping-selective hydrogen combustion (CL-SHC), and provides a supported polymetallic oxide tandem catalyst, and a preparation method and application thereof, wherein the catalyst may couple a direct propane dehydrogenation (PDH) site and a selective hydrogen combustion site at nano-scale, wherein an oxide of metal A (V, Cr, Zn, or Ga) serves as the direct dehydrogenation catalytic site, while metal vanadate $MVO_4$ (M=Fe, Bi, or Mn) nano-particles serve as the selective hydrogen combustion site. According to the present disclosure, the direct propane dehydrogenation site and a selective hydrogen combustion site are coupled at the nano-scale. This coupling mechanism shifts the reaction equilibrium to the right through the selective combustion of byproduct hydrogen, which effectively surpasses the thermodynamic limit; and meanwhile, the combustion of hydrogen releases chemical energy, and provides heat energy through direct heating, enabling the self-heating operation of the reaction. The present disclosure has the outstanding advantages of high single-pass conversion rate of light alkanes and high selectivity towards target product alkenes.

To solve the above technical problems, the present disclosure is achieved by the following technical solutions:

According to one aspect of the present disclosure, a supported polymetallic oxide tandem catalyst is provided, including a support, wherein a surface of the support is supported with an oxide of metal A and then with metal vanadate nano-particles; and the oxide of metal A serves as a direct dehydrogenation catalytic site, and the metal vanadate nano-particles serve as a selective hydrogen combustion site;

- wherein, the oxide of metal A is vanadium oxide or chromium oxide which is sub-monodispersed on the surface of the support, or zinc oxide nano-particles or gallium oxide nano-particles which are uniformly loaded on the surface of the support; and
- metal M in the metal vanadate is selected from one of Fe, Bi, and Mn.

Further, the support is $Al_2O_3$, $SiO_2$, $TiO_2$, or a molecular sieve.

Further, a mass of the metal A is 1 to 10 wt. % of a total mass of the catalyst, and a mass of the metal vanadate is 10 to 50 wt. % of the total mass of the catalyst.

Further, a particle size of the metal vanadate nano-particles ranges from 100 nm to 200 nm, and a particle size of the zinc oxide nano-particles or the gallium oxide nano-particles ranges from 2 nm to 5 nm.

According to another aspect of the present disclosure, a preparation method of the supported polymetallic oxide tandem catalyst is provided, which includes the following steps:

(1) dissolving a precursor salt of the metal A in deionized water and impregnating the precursor salt on the surface of the support, wherein the metal A is selected from one of V, Cr, Zn, and Ga;

(2) drying the impregnated carrier, and then roasting the support in air at a temperature of 500-700° C. to obtain catalyst, the roasted catalyst is for standby use;

(3) dissolving a precursor salt of the metal M in the deionized water, and uniformly mixing with dissolved vanadium precursor salt; heating and evaporating the mixed solution in a water bath to dryness to obtain the metal vanadate; wherein the metal M is selected from one of Fe, Bi, and Mn;

(4) drying the substance obtained in step (3), and roasting the substance in the air at the temperature of 500-700° C. for standby use;

(5) dispersing the metal vanadate obtained in step (4) in an aqueous solution, and impregnating the metal vanadate in the catalyst obtained in step (2); and (6) drying the substance obtained in step (5), roasting the substance in the air at the temperature of 500-700° C. to obtain tandem catalyst, and tableting and sieving the roasted tandem catalyst for standby use.

Further, the precursor salt of the metal A in step (1) is one of a mixture of ammonium metavanadate and a complexing agent, chromium nitrate, zinc nitrate or gallium nitrate; and the precursor salt of the metal M in step (3) is one of ferric nitrate, bismuth nitrate or manganese nitrate, and the vanadium precursor salt is the mixture of the ammonium metavanadate and the complexing agent.

Further, in steps (2), (4) and (6), the drying temperature is 80-100° C. and the drying time is 6-12 hours, and the roasting time is 1-8 hours.

According to another aspect of the present disclosure, an application of the supported polymetallic oxide tandem catalyst as mentioned above in light alkane dehydrogenation and chemical looping-selective hydrogen combustion is provided. The tandem catalyst reacts with light alkanes in the absence of co-feed of oxygen, and the oxide of metal A serves as the direct dehydrogenation catalytic site for converting the light alkanes into corresponding alkenes and hydrogen; the metal vanadate nano-particles serve as selective hydrogen combustion site for selectively combusting byproduct hydrogen to generate product water and release heat energy, and the metal vanadate is reduced to a low valence state; oxygen or air is introduced into the reacted tandem catalyst for regenerating the catalyst, lattice oxygen of low-valence metal vanadate is supplemented, and meanwhile, carbon deposits are combusted to release heat energy; and after the above cycle, the tandem catalyst returns to an original state.

Further, the number of carbon atoms of the light alkanes ranges from 2 to 4.

Further, the supported polymetallic oxide tandem catalyst and quartz sand are mixed physically and evenly at a mass ratio of (0.2-1):1, a reaction is carried out under normal pressure and at a reaction temperature of 450-650° C., and before the reaction, nitrogen is introduced to remove air, followed by introducing propane; wherein a total flow of the propane and the nitrogen is 20-50 mL/min, and the volume percentage of the propane is 5-30%.

The present disclosure has the following beneficial effects:

According to the supported polymetallic oxide tandem catalyst of the present disclosure, a double-catalytic site structure is constructed on the nano-scale, and the direct propane dehydrogenation site and the chemical looping-selective hydrogen combustion site are organically coupled on the nano-scale. This coupling shifts the reaction equilibrium to the right through the selective combustion of the byproduct hydrogen, which effectively surpasses the thermodynamic limit; and meanwhile, the combustion of hydrogen releases chemical energy, and provides heat energy through direct heating, enabling the self-heating operation of the reaction. Wherein, the oxide of metal A (V, Cr, Zn, or Ga) serves as the direct dehydrogenation catalytic site of light alkanes, and the lattice oxygen in the metal vanadate $MVO_4$ (M=Fe, Bi, or Mn) nano-particles in a bulk phase participates in the selective hydrogen combustion to produce product water; and additionally, the supported polymetallic oxide tandem catalyst of the present disclosure enables the participation of the oxide of the metal A (V, Cr, Zn, or Ga) loaded on the surface of the carrier in the direct dehydrogenation reaction, while maintaining a high conversion rate and selectivity, even after the consumption of the lattice oxygen in the metal vanadate $MVO_4$ (M=Fe, Bi, or Mn) nano-particles in the bulk phase. Meanwhile, the introduction of a vanadium element into the metal vanadate $MVO_4$ (M=Fe, Bi, or Mn) nano-particles in the bulk phase constructs the metal vanadate, effectively solving the problems of sintering and deactivation of pure ferric oxide, bismuth oxide, and the like during an oxidation-reduction process due to the loss of metal bismuth.

The preparation method of the supported polymetallic oxide tandem catalyst adopts an impregnation method, and is cost-effective, simple in operation and likely to be produced on a large scale; and meanwhile, the oxides with low cost, high availability and rich reserves are adopted.

The supported polymetallic oxide tandem catalyst is applied to light alkane dehydrogenation and CL-SHC, and has the outstanding advantages of single-pass high conversion rate of light alkanes and high selectivity of target product alkenes; the catalyst with the optimal propylene yield can be obtained by adjusting support selection, loading capacity and the double-site coupling method; the reaction equilibrium is shifted to the right through the selective combustion of the byproduct hydrogen, which effectively surpasses the thermodynamic limit; and meanwhile, the combustion of hydrogen releases chemical energy, and provides heat energy through direct heating, enabling the self-heating operation of the reaction. Meanwhile, the problems of the sintering and deactivation of pure ferric oxide and bismuth oxide in the oxidation-reduction process can be effectively solved, and the performance and the structure of the catalyst can be kept stable after a plurality of reduction-oxidation regeneration cycles. Oxygen or air is introduced into the catalyst that has undergone the reaction for regeneration, so that the lattice oxygen of the low-valence catalyst is supplemented; and meanwhile, carbon deposits are effectively combusted, heat arising therefrom is transferred through the catalyst as a medium, and high heat matching can be achieved by adjusting the mass of the catalyst. Compared with the prior art, the direct participation of oxygen is prevented, the high cost of air separation is saved, the generation of deep oxidation products is reduced, and the potential safety hazard of blending reducing and oxidizing gases is eliminated.

DETAILED DESCRIPTION OF THE PRESENT DISCLOSURE

Figure 1:
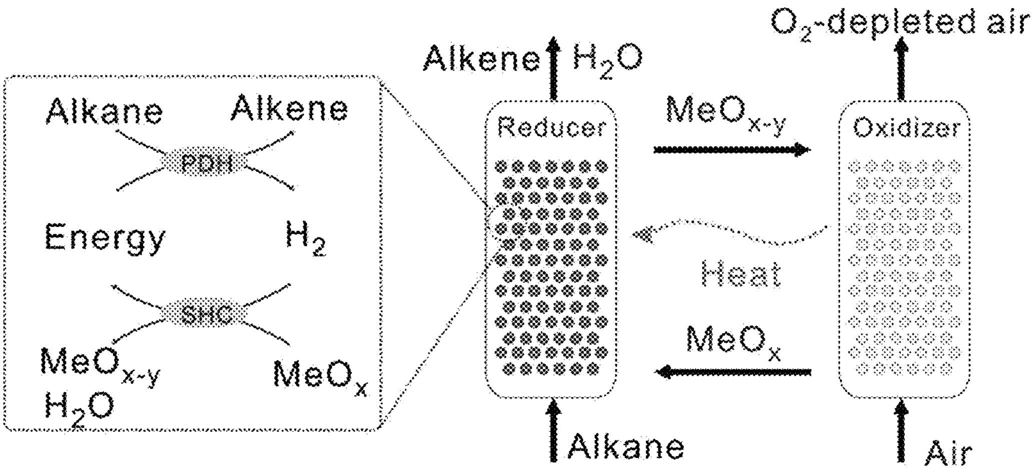
FIG. 1 a schematic diagram illustrating a process of coupling light alkane direct dehydrogenation with CL-SHC according to the present disclosure.

The present disclosure is further described in detail below through specific embodiments, and the following embodiments can allow those skilled in the art to understand the present disclosure more comprehensively, instead of limiting it in any manner.

Embodiment 1

Step 1, mixing 0.07 parts by mass of ammonium metavanadate with 0.15 parts by mass of oxalic acid evenly, and dissolving a mixture in 2.0 mL of deionized water to form an impregnating solution. Wherein, a complexing agent may also be citric acid and the like, besides oxalic acid;

Step 2, impregnating the impregnating solution obtained in step 1 onto a surface of 1.0 part by mass of $Al_2O_3$ carrier in equal volume, and drying at a temperature of 80-100° C. for 6 to 12 hours;

Step 3, roasting the substance obtained in step 2 in a muffle furnace under an air atmosphere at a temperature of 500° C. for 1 to 8 hours to obtain a vanadium oxide catalyst loaded on aluminum oxide; and the percentage content of metal vanadium is 3% by mass based on a total mass of the tandem catalyst, and a molecular formula is denoted as 3V/Al. The roasted catalyst is naturally cooled to a room temperature for standby use;

Step 4, mixing 5.0 parts by mass of ferric nitrate with 2.5 parts by mass of citric acid evenly, dissolving a mixture in 200.0 mL of deionized water to form a solution-1, wherein a complexing agent may also be oxalic acid and the like, besides the citric acid;

dissolving 1.5 parts by mass of ammonium metavanadate in 200.0 mL of deionized water evenly to form a solution-2;

adding the solution-2 to the solution-1, stirring, and water-bathing a mixed solution at a temperature of 100° C. for 3 to 4 hours, and evaporating the solution to dryness, and then drying at a temperature of 80-100° C. for 6 to 12 hours to obtain a substance;

roasting the substance in the muffle furnace under the air atmosphere at a temperature of 500° C. for 1 to 8 hours to obtain a catalyst, and a molecular formula of the obtained catalyst is denoted as $FeVO_4$;

Step 5, impregnating the $FeVO_4$ prepared in step 4 onto the catalyst obtained in step 3, and drying at a temperature of 80-100° C. for 6 to 12 hours to obtain a substance; and roasting the substance in the muffle furnace under the air atmosphere at a temperature of 500° C. for 1 to 8 hours to obtain a tandem catalyst.

The percentage content of the $FeVO_4$ is 30% by mass based on the total mass of the tandem catalyst, and a molecular formula is denoted as 30FeV-3V/Al.

Step 6, naturally cooling the roasted tandem catalyst to a room temperature, and obtaining a granular catalyst at 20-40 meshes by being tableted, and sieved. The sieved 30FeV-3V/Al tandem catalyst is put into a fixed bed reactor, and reaction gas is introduced for reaction, wherein the reaction gas is propane, and balance gas is nitrogen.

Embodiment 2

The preparation and reaction are carried out through the method as shown in Embodiment 1, only except that 0.25 parts by mass of chromium nitrate is evenly dissolved in 2.0 mL of deionized water to form an impregnating solution in step 1. The percentage content of $FeVO_4$ is 30% by mass based on the total mass of a tandem catalyst, and a molecular formula is denoted as 30FeV-3Cr/Al.

Embodiment 3

The preparation and reaction are carried out through the method as shown in Embodiment 1, only except that 0.14 parts by mass of zinc nitrate is evenly dissolved in 2.0 mL of deionized water to form an impregnating solution in step 1. The percentage content of $FeVO_4$ is 30% by mass based on the total mass of a tandem catalyst, and a molecular formula is denoted as 30FeV-3Zn/Al.

Embodiment 4

The preparation and reaction are carried out through the method as shown in Embodiment 1, only except that 0.12 parts by mass of gallium nitrate is evenly dissolved in 2.0 mL of deionized water to form an impregnating solution in step 1. The percentage content of $FeVO_4$ is 30% by mass based on the total mass of a tandem catalyst, and a molecular formula is denoted as 30FeV-3Ga/Al.

Embodiment 5

The preparation and reaction are carried out through the method as shown in Embodiment 1, only except those calcination temperatures in steps 3, 4 and 5 are 600° C.

Embodiment 6

The preparation and reaction are carried out through the method as shown in Embodiment 1, only except those calcination temperatures in steps 3, 4 and 5 are 700° C.

Embodiment 7

The preparation and reaction are carried out through the method as shown in Embodiment 1, only except those calcination temperatures in steps 3, 4 and 5 are 400° C.

Embodiment 8

The preparation and reaction are carried out through the method as shown in Embodiment 1, only except those calcination temperatures in steps 3, 4 and 5 are 800° C.

Embodiment 9

The preparation and reaction are carried out through the method as shown in Embodiment 1, only except that 0.02 parts by mass of ammonium metavanadate and 0.05 parts by mass of complexing agent are evenly mixed and dissolved in 2.0 mL of deionized water to form an impregnating solution in step 1, wherein the complexing agent is oxalic acid or citric acid. A molecular formula of a tandem catalyst is denoted as 30FeV-1V/Al.

Embodiment 10

The preparation and reaction are carried out through the method as shown in Embodiment 1, only except that 0.25 parts by mass of ammonium metavanadate and 0.55 parts of complexing agent are evenly mixed and dissolved in 2.0 mL of deionized water to form an impregnating solution in step 1, wherein the complexing agent is oxalic acid or citric acid. A molecular formula of a tandem catalyst is denoted as 30FeV-10V/Al.

Embodiment 11

The preparation and reaction are carried out through the method as shown in Embodiment 1, only except that in step 1, 0.6 parts by mass of ammonium metavanadate and 1.2 parts by mass of complexing agent are evenly mixed and dissolved in 2.0 mL of deionized water to form an impregnating solution, wherein the complexing agent is oxalic acid or citric acid. A molecular formula of a tandem catalyst is denoted as 30FeV-20V/Al.

Embodiment 12

The preparation and reaction are carried out through the method as shown in Embodiment 1, only except that the percentage content of $FeVO_4$ is 10% by mass based on the total mass of a tandem catalyst, and a molecular formula is denoted as 10FeV-3V/Al.

Embodiment 13

The preparation and reaction are carried out through the method as shown in Embodiment 1, only except that the percentage content of $FeVO_4$ is 50% by mass based on the total mass of a tandem catalyst, and a molecular formula is denoted as 50FeV-3V/Al.

Embodiment 14

The preparation and reaction are carried out through the method as shown in Embodiment 1, only except that the percentage content of $FeVO_4$ is 70% by mass based on the total mass of a tandem catalyst, and a molecular formula is denoted as 70FeV-3V/Al.

Embodiment 15

The preparation and reaction are carried out through the method as shown in Embodiment 1, only except that in step 2, the impregnating solution obtained in step 1 is impregnated onto 1.0 part by mass of $SiO_2$ carrier in an equal volume. A molecular formula of a tandem catalyst is denoted as 30FeV-3V/Si.

Embodiment 16

The preparation and reaction are carried out through the method as shown in Embodiment 1, only except that in step 2, the impregnating solution obtained in step 1 is impregnated onto 1.0 part by mass of $TiO_2$ carrier in an equal volume. A molecular formula of a tandem catalyst is denoted as 30FeV-3V/Ti.

Embodiment 17

The preparation and reaction are carried out through the method as shown in Embodiment 1, only except that in step 2, the impregnating solution obtained in step 1 is impregnated onto 1.0 part by mass of molecular sieve carrier in an equal volume. A molecular formula of a tandem catalyst is denoted as 30FeV-3V/Zeolite.

Embodiment 18

The preparation and reaction are carried out through the method as shown in Embodiment 1, only except that in step 4, 6.2 parts by mass of bismuth nitrate and 2.5 parts by mass of citric acid are evenly mixed and dissolved in 200.0 mL of deionized water to form a solution-1, wherein the obtained catalyst is based on the total mass of the tandem catalyst, the percentage content of $BiVO_4$ is 30% by mass, and a molecular formula is denoted as 30BiV-3V/Al.

Embodiment 19

The preparation and reaction are carried out through the method as shown in Embodiment 1, only except that in step 4, 4.6 parts by mass of aqueous solution of manganous nitrate and 2.5 parts by mass of citric acid are evenly mixed and dissolved in 200.0 mL of deionized water to form a solution-1, wherein the obtained catalyst is based on the total mass of the tandem catalyst, the percentage content of $MnVO_4$ is 30% by mass, and a molecular formula is denoted as 30MnV-3V/Al.

Embodiment 20

In step 1, 0.2-0.8 g of tandem catalysts obtained in any one of Embodiments 1-19 are weighed respectively and mixed with quartz Sand (SiC), and the experiment is carried out in a fixed bed tubular reactor at a reaction temperature of 450-600° C. and 1 atmospheric pressure. Before the reaction, $N_2$ is introduced into the tubular reactor to evacuate oxygen and air, and then, propane is introduced therein, wherein the total flow of the propane and the nitrogen is 20 mL/min, and the volume percentage of the propane is 10%. The composition of the product is tested by gas chromatography.

The propane conversion rate is calculated from the following formula:

$$X_{C_3H_6} = \frac{F^{in}_{C_3H_6} - F^{out}_{C_3H_6}}{F^{in}_{C_3H_6}}$$

Where, $X_{C_3H_6}$ represents propane conversion rate, %

$$F^{in}_{C_3H_6}$$

represents molar flow of propane at reactor inlet, moL/min $$F^{out}_{C_3H_6}$$

represents molar flow of propane at reactor outlet, moL/min;

The gaseous phase selectivity of the product is calculated from the following formula:

$$S_{Product\ A} = \frac{n_{Product\ A}}{\sum n_{product}} = x_{Product\ A}$$

Where, ${}^{s}_{product\ A}$ represents selectivity of gaseous product A, %

${}^{s}_{product\ A}$ represents yield of gaseous product A, moL $\Sigma n_{product}$ represents sum of amounts of all gaseous products, moL $x_{product\ A}$ represents content of gaseous product A in all gaseous products The gaseous product A includes $C_3H_6$, COx (oxycarbide, i.e., CO, and $CO_2$), $CH_4$, $C_2H_6$, and $C_2H_4$.

As shown in FIG. 1, according to a process of coupling direct PDH with CL-SHC, the lattice oxygen was recycled and supplemented through a metal oxide-based tandem catalyst serving as a medium, and oxygen removal from a crystal lattice and effective separation from the crystal lattice in the supplementation process may be achieved spatially or temporally. At the reaction stage, a light alkane dehydrogenation site was converted into corresponding alkenes and hydrogen; the reaction balance was shifted to the right through the selective combustion of byproduct hydrogen at a selective hydrogen combustion site, which effectively surpassed the thermodynamic limit; and meanwhile, the combustion of hydrogen released chemical energy, and provided heat energy through direct heating, enabling the self-heating operation of the reaction. Oxygen or air was introduced into the catalyst that has undergone the reaction for regeneration, so that the lattice oxygen of a low-valence oxygen carrier was supplemented; and meanwhile, carbon deposits were effectively combusted, heat arising therefrom was transferred through the oxygen carrier as a medium, and high heat matching may be achieved by adjusting the mass of the oxygen carrier. The supported polymetallic oxide tandem catalyst of the present disclosure is applied to the process of coupling light alkane dehydrogenation with CL-SHC. Taking a chemical looping propane dehydrogenation reaction as an example, a catalyst and quartz sand which are evenly and physically mixed are filled into a reaction bed, and before the reaction, nitrogen is introduced to remove air, and then, propane is introduced, wherein the total flow of the propane and the nitrogen is 20-50 ml/min, and the volume percentage of the propane is 5-30%. The performance of the catalyst is examined at normal pressure and a reaction temperature of 450-650° C.

Figure 2:
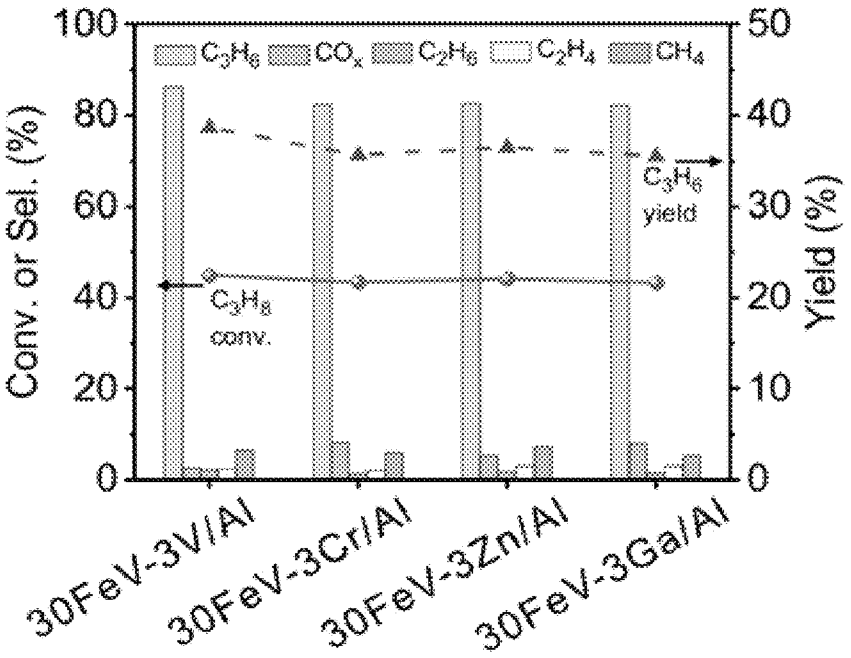
FIG. 2 is a diagram illustrating propane conversion rate, product selectivity, and propylene yield of tandem catalysts prepared in Embodiments 1-4 during chemical looping propane dehydrogenation.

As shown in FIG. 2, a solid line dot plot represents a propane conversion, a bar graph shows product selectivity, and a dashed line triangle plot represents a propylene yield. Seen from FIG. 2, the supported polymetallic oxide tandem catalyst greatly improved the selectivity for propylene. The 30FeV-3V/Al may achieve the single-pass yield of the propylene as high as 40%, and the essential reason for the improved selectivity is that the supported tandem catalyst achieves the effective coupling of the PDH catalytic site and the selective hydrogen combustion site at a nano-scale, so that the catalyst may still maintain a higher conversion and selectivity after the consumption of the lattice oxygen. It should be noted that if the catalyst that is conducive to combusting hydrogen is effectively coupled at the catalytic site with the excellent dehydrogenation ability, the tandem catalysis of PDH and selective hydrogen combustion will be achieved at the nano-scale. According to the comparison between embodiments, the tandem catalyst has the better effect in terms of calcination temperature of 500-700° C. and the mass of metal A accounting for 1-10 wt. % of the total mass of the catalyst.

Figure 3:
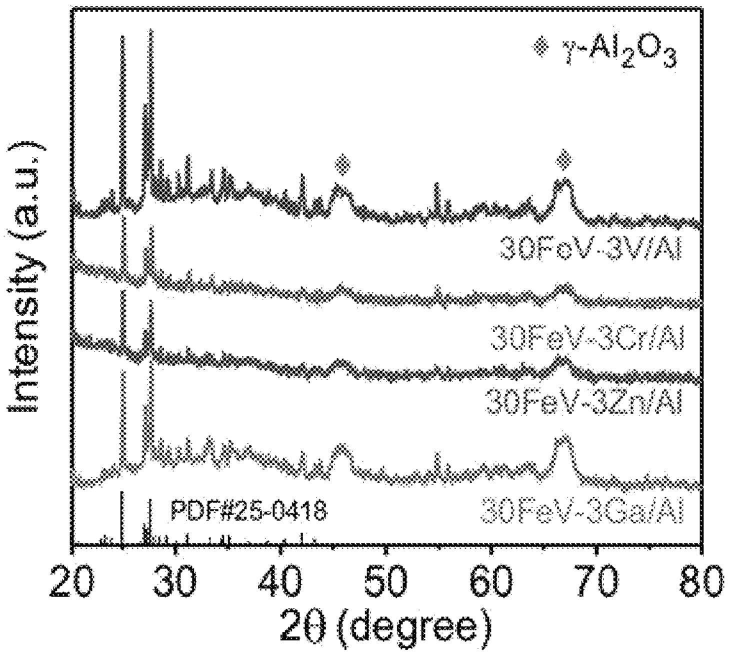
FIG. 3 is a spectrogram illustrating results of X-ray diffraction (XRD) tests of tandem catalysts prepared in Embodiments 1-4 according to the present disclosure.

The fresh tandem catalysts prepared in the above embodiments are analyzed through XRD results, and results are shown in FIG. 3. When the catalysts were loaded on the supports, 30FeV-3V/Al, 30FeV-3Cr/Al, 30FeV-3Zn/Al and 30FeV-3Ga/Al all showed similar effects to XRD characteristic peaks of pure $FeVO_4$ and gamma-$Al_2O_3$, the XRD characteristic peaks of oxides of vanadium, chromium, zinc and gallium were not found, indicating that the oxides of vanadium, chromium, zinc and gallium were uniformly dispersed on the surfaces of the supports, and meanwhile, the crystal structures of the catalysts were not changed under the higher loading capacity of the metal vanadate.

Figure 4:
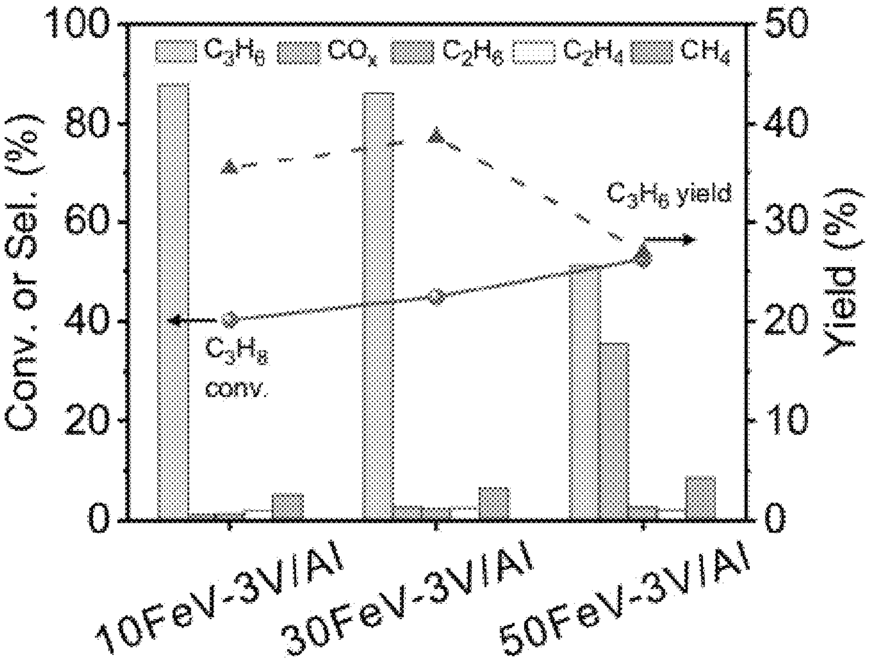
FIG. 4 is a diagram illustrating propane conversion rate, product selectivity, and propylene yield of tandem catalysts prepared in Embodiments 1, 12, and 13 during chemical looping propane dehydrogenation.
Figure 5:
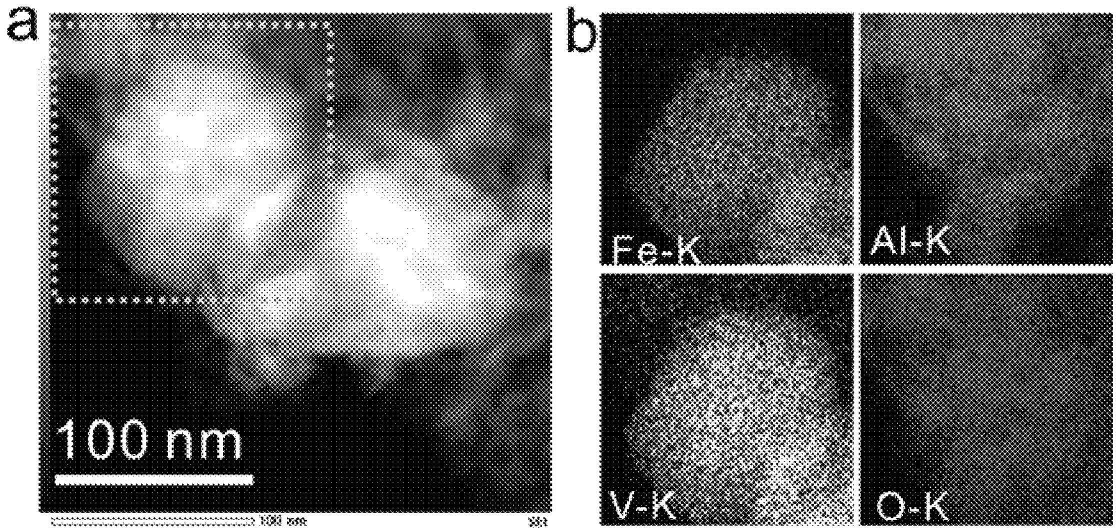
FIG. 5 shows a: a high angle angular dark field-scanning transmission electron microscopy (HAADF-STEM) map and b: an energy dispersive spectroscopy mapping (EDS-MAPPING) map of a 30FeV-3V/Al tandem catalyst prepared in Embodiment 1 according to the present disclosure, showing distribution diagrams of an Al element, an O element, an Fe element and a V element, wherein a scale of the HAADF-STEM map is 100 nm.

According to the comparison between embodiments, the metal vanadate has the better effect in terms of the mass accounting for 10-50 wt. % of the total mass of the catalyst. The loading capacity of $FeVO_4$ onto 3V/Al was changed, and as can be known from the performance test results of FIG. 4, the performance of 30FeV-3V/Al was the best. We will further explore the microstructure thereof. FIG. 5 shows an HAADF-STEM and an EDS-MAPPING of a 30FeV-3V/Al tandem catalyst, showing that the ferric vanadate has a grain size of approx. 100-200 nm and is of a solid solution structure, and the tests are consistent with XRD results. The vanadium oxide was sub-monodispersed on the surface of the support and served as a catalytic site for the direct PDH, and the vanadium oxide and the adjacent ferric vanadate grains cooperated with each other to achieve the tandem catalysis at the nano-scale.

Figure 6:
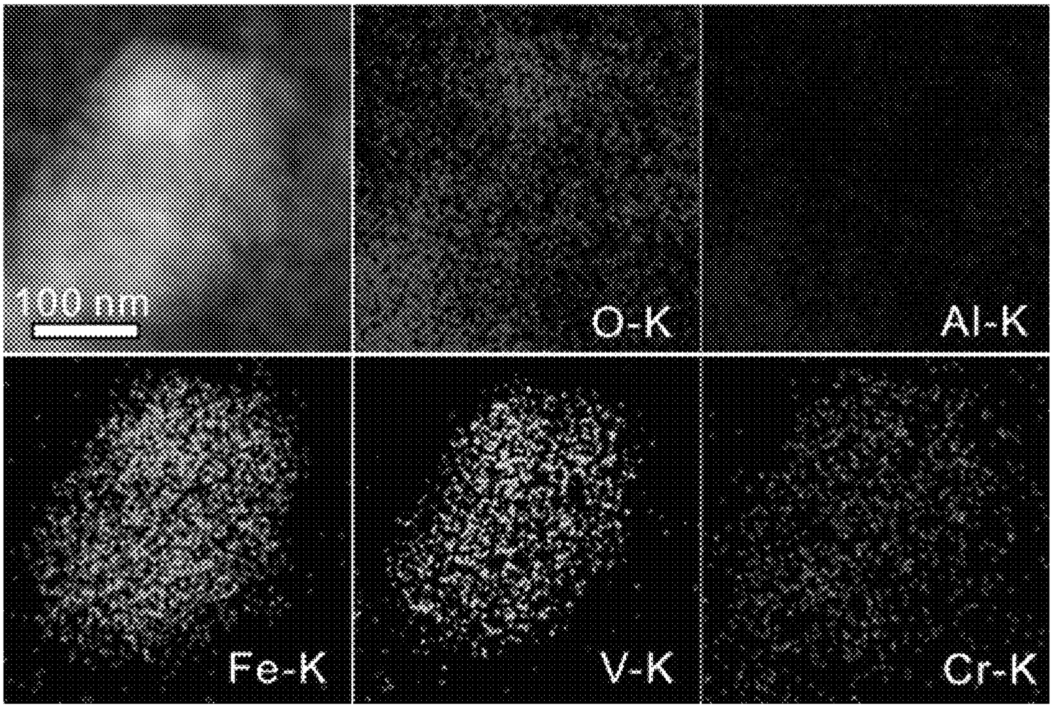
FIG. 6 is an HAADF-STEM map and an EDS-MAPPING map illustrating a 30FeV-3Cr/Al tandem catalyst prepared in Embodiment 2 according to the present disclosure.
Figure 7:
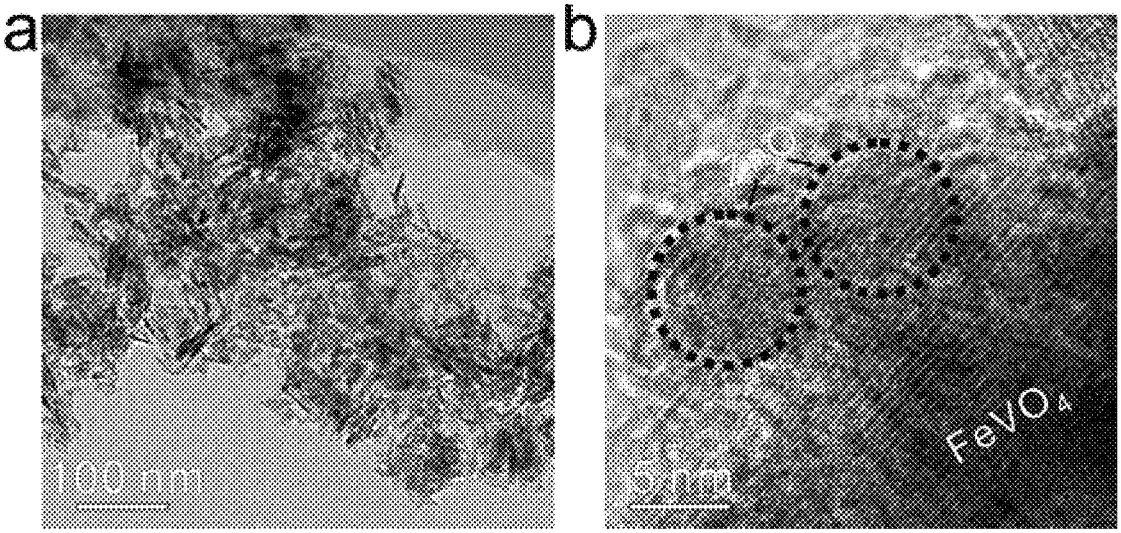
FIG. 7 is a TEM mapping illustrating a 30FeV-3Zn/Al tandem catalyst prepared in Embodiment 3 according to the present disclosure.

The microstructure of 30FeV-3Cr/Al prepared in Embodiment 2 is further investigated. FIG. 6 shows an HAADF-STEM and EDS-MAPPING map of a 30FeV-3Cr/Al tandem catalyst, showing that the ferric vanadate has a grain size of approx. 100-200 nm and is of a solid solution structure, and the tests are consistent with XRD results. The chromium oxide was sub-monodispersed on the surface of the support and served as the catalytic site for the PDH, and the chromium oxide and the adjacent ferric vanadate grains cooperated with each other to achieve the tandem catalysis on the nano-scale. The microstructure of 30FeV-3Zn/Al prepared in Embodiment 3 is further investigated. FIG. 7 shows a TEM map of a 30FeV-3Zn/Al tandem catalyst, showing that the ferric vanadate has a grain size of approx. 100-200 nm and is of a solid solution structure, and the tests are consistent with XRD results. The zinc oxide was sub-monodispersed on the surface of the carrier in the form of nano-particles sized 2-5 nm and served as the catalytic site for the PDH, and the zinc oxide and the adjacent ferric vanadate grains cooperated with each other to achieve the tandem catalysis at the nano-scale.

Figure 8:
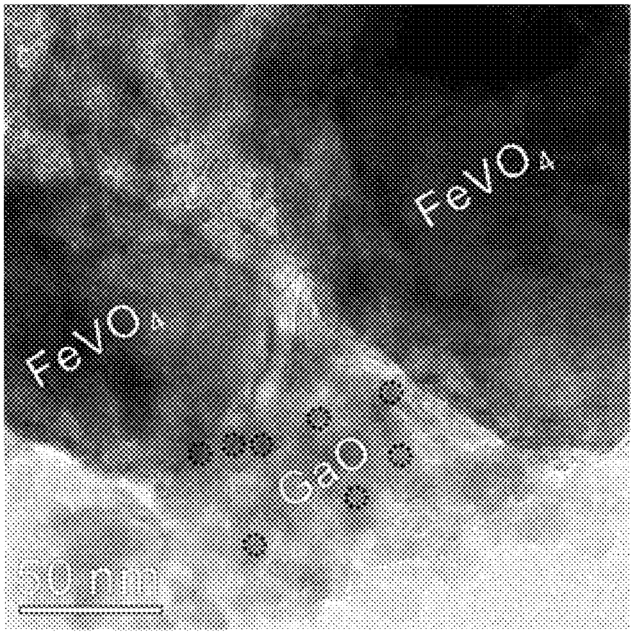
FIG. 8 is a TEM mapping illustrating a 30FeV-3Ga/Al tandem catalyst prepared in Embodiment 4 according to the present disclosure.
Figure 9:
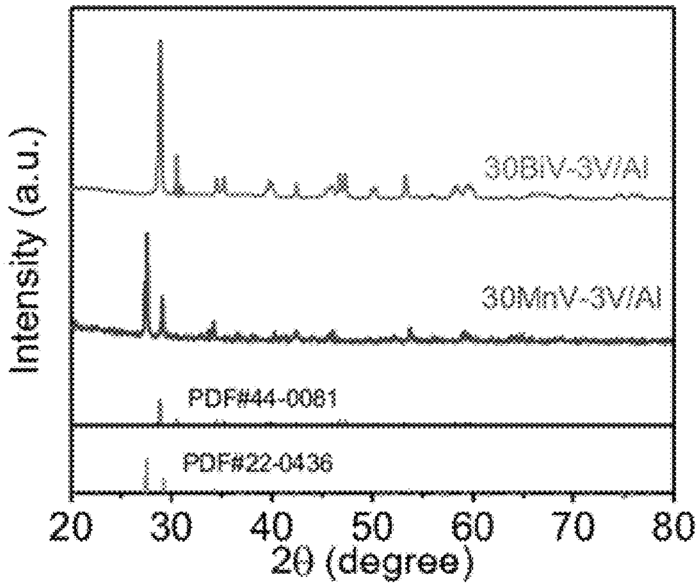
FIG. 9 is a spectrogram illustrating results of XRD tests of tandem catalysts prepared in Embodiments 18 and 19 according to the present disclosure.

The microstructure of 30FeV-3Ga/Al prepared in Embodiment 4 is further investigated. FIG. 8 shows a TEM map of a 30FeV-3Ga/Al tandem catalyst, showing that the ferric vanadate has a grain size of approx. 100-200 nm and is of a solid solution structure, and the tests are consistent with XRD results. The gallium oxide was dispersed on the surface of the carrier in the form of nano-particles sized 2-5 nm and served as the catalytic site for the PDH, and the gallium oxide and the adjacent ferric vanadate grains cooperated with each other to achieve the tandem catalysis on the nano-scale. Experimental research shows that the nano-scale tandem catalyst is equally effective on other supported metal vanadates. As shown in Embodiments 18 and 19, the tandem catalyst may be extended to the metal vanadates, such as bismuth vanadate, and manganese vanadate. As shown in FIG. 9, the 30BiV-3V/Al shows the similar effect to the XRD characteristic peaks of the pure bismuth vanadate and the gamma-$Al_2O_3$; and the 30MnV-3V/Al shows the similar effect to the XRD characteristic peaks of the pure manganese vanadate and the gamma-$Al_2O_3$. This indicates that the crystal structure of the catalyst is not changed at the higher loading capacity of the metal vanadates.

Although the preferred embodiments of the present disclosure are described above with reference to the drawings, the present disclosure is not limited to the above specific implementations, and the above specific implementations are only schematic instead of restrictive. Those ordinarily skilled in the art may also make many forms of specific transformations without departing from the purpose of the present disclosure and the scope protected by the claims under the inspiration of the present disclosure, and these transformations all belong to the protection scope of the present disclosure.

What is claimed is:

1. A supported polymetallic oxide tandem catalyst, comprising a support, wherein a surface of the support is supported with an oxide of metal A and then with metal vanadate nano-particles; and the oxide of metal A serves as a direct dehydrogenation catalytic site, and the metal vanadate nano-particles serve as a selective hydrogen combustion site;

wherein, the oxide of metal A is vanadium oxide or chromium oxide which is sub-monodispersed on the surface of the support, or zinc oxide nano-particles or gallium oxide nano-particles which are uniformly loaded on the surface of the support; and metal M in the metal vanadate is selected from one of Fe, Bi, and Mn; and wherein a particle size of the metal vanadate nano-particles ranges from 100 nm to 200 nm, and a particle size of the zinc oxide nano-particles or the gallium oxide nano-particles ranges from 2 nm to 5 nm.

2. The supported polymetallic oxide tandem catalyst according to claim 1, wherein the support is $Al_2O_3$, $SiO_2$, $TiO_2$, or a molecular sieve.

3. The supported polymetallic oxide tandem catalyst according to claim 1, wherein a mass of the metal A is 1 to 10 wt. % of a total mass of the catalyst, and a mass of the metal vanadate is 10 to 50 wt. % of the total mass of the catalyst.

* * * * *